United States Patent [19]

Yamazaki et al.

[11] Patent Number: 4,902,131
[45] Date of Patent: Feb. 20, 1990

[54] SURFACE INSPECTION METHOD AND APPARATUS THEREFOR

[75] Inventors: Yuichiro Yamazaki, Yokohama; Motosuke Miyoshi, Fujisawa; Shigeru Ogawa; Katsuya Okumura, both of Yokohama, all of Japan

[73] Assignee: Kabushiki Kaisha Toshiba, Kawasaki, Japan

[21] Appl. No.: 844,601

[22] Filed: Mar. 27, 1986

[30] Foreign Application Priority Data

Mar. 28, 1985 [JP] Japan .................................. 60-64896
Dec. 10, 1985 [JP] Japan ................................ 60-277545

[51] Int. Cl.$^4$ ............................................ G01N 21/01
[52] U.S. Cl. .................................. 356/336; 356/237
[58] Field of Search .............. 356/336, 337, 338, 446, 356/237; 357/336, 337, 338, 446

[56] References Cited

U.S. PATENT DOCUMENTS

| | | | |
|---|---|---|---|
| 3,229,564 | 1/1966 | Meltzer | 356/446 |
| 3,340,400 | 9/1967 | Quittner | 250/562 |
| 4,285,597 | 8/1981 | Lamprecht et al. | 356/446 |
| 4,352,017 | 9/1982 | Duffy et al. | 250/358.1 |
| 4,360,275 | 11/1982 | Louderback | 356/446 |

FOREIGN PATENT DOCUMENTS 49060 11/1968 German Democratic Rep. .
826156 12/1959 United Kingdom .
2009922 6/1979 United Kingdom .

OTHER PUBLICATIONS

Preprint of 32nd Lectures of the Japan Society of Applied Physics, 29a—A—3 "Development of Dust Detecting Apparatus; Detection of Dust on a Wafer with Thin Film", Yamazaki et al., published Mar. 29, 1985.

Primary Examiner—Richard A. Rosenberger
Attorney, Agent, or Firm—Foley & Lardner, Schwartz, Jeffery, Schwaab, Mack, Blumenthal & Evans

[57] ABSTRACT

A novel technique suitable for inspection or examination of the surface condition of a substrate such as a semiconductor wafer. First is one irradiates a light e.g. a laser beam on a substrate surface to focus a scattered light therefrom. Next detects the scattered light focused e.g. with a photomultiplier tube, thus to inspect the substrate surface. When the detection of the scattered light is thus carried out, correction means e.g. a circuit for controlling a voltage applied to the photomultiplier tube, a filter having a variable light-screening factor, a movable iris or an amplification factor adjustment circuit etc. is used to correct the detection sensitivity in accordance with the reflectivity of the substrate surface. Practically, such a corrective operation is carried out on the basis of the intensity of a scattered light or a regularly reflected light from the substrate surface. Further, it may be possible to obtain a signal for control of the corrective operation by averaging signals detected when the substrate surface is subject to scanning of an irradiating light. Thus, this surface inspection technique can detect particles attached on the substrate surface always utilizing the same slice level and the same sensitivity even when substrates having different indices of reflection are employed.

17 Claims, 8 Drawing Sheets

SURFACE INSPECTION METHOD AND APPARATUS THEREFOR

BACKGROUND OF THE INVENTION

The present invention relates to a method and an apparatus for inspecting the surface of a substrate e.g. a semiconductor wafer etc. on the basis of a scattered light from dust or rubbish etc. on the substrate surface.

In the fabrication of semiconductor devices, one generally detects particles attached on the surface of the semiconductor wafer in order to improve yield of semiconductor chips obtained from a semiconductor wafer. Hitherto, such a detection is achieved by irradiating a laser beam etc. on the surface of a substrate e.g. a semiconductor wafer etc. to focus a scattered light from the substrate surface to detect the scattered light thus focused by using a photo-multiplier tube. For instance, where the substrate is a silicon wafer, since an output voltage based on a scattered light from particles on the substrate monotonously increases as indicated by the sensitivity characteristic curve A in FIG. 18, detection is made by setting a slice level to a level with respect to a particular particle diameter, thus to judge the particle diameter on the basis of the output voltage of the photo-multiplier tube.

Figure 18:
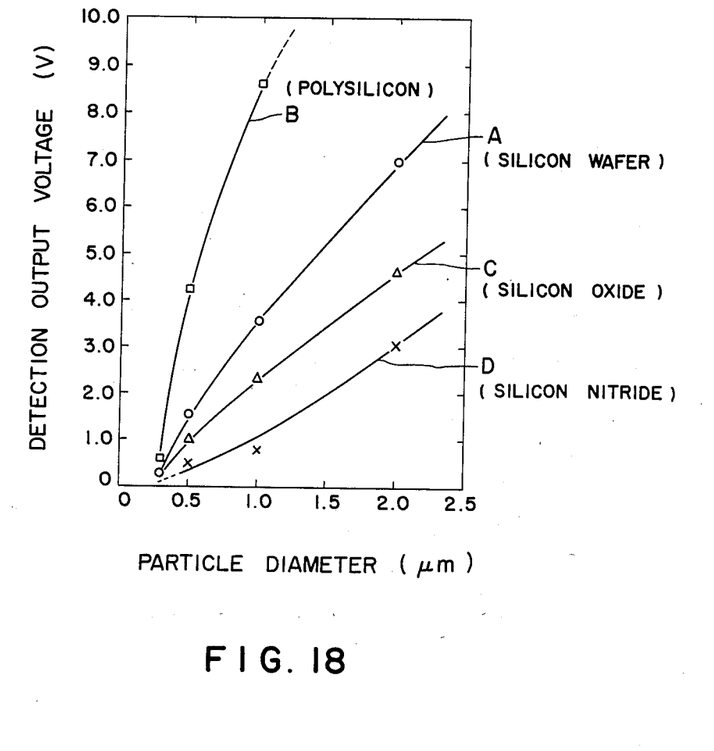
FIG. 18 is a graph showing detection output voltage versus particle diameter measured in respect to each of various substrates.

However, in the case where thin films of other compounds are formed on the surface of the silicon wafer, it is difficult to determine such slice levels. The sensitivity characteristic curve B in FIG. 18 shows the case where a polysilicon thin film is formed on the surface of the silicon wafer. Likewise, sensitivity characteristic curves C and D show the cases where thin films of a silicon oxide and a silicon nitride are formed thereon, respectively. Because the optical properties, particularly reflectivity or reflection factor characteristics of respective thin films are different from each other, each sensitivity characteristic curve differs from that of the silicon wafer, with the result that one becomes difficult to determine the slice level and it is unable to detect particles with the same sensitivity as that measured with the silicon wafer.

SUMMARY OF THE INVENTION

An object of the present invention is to provide a surface inspection method and an apparatus therefor making it possible to detect particles with the same slice level and the same sensitivity even when substrates having different indices of reflection are employed.

The above-mentioned object is realized by a surface inspection method comprising the steps of irradiating a light on the surface of a substrate, focusing a scattered light from the substrate surface, and detecting the scattered light focused, thus to inspect the substrate surface, characterized in that a detection sensitivity of a scattered light is corrected on the basis of a reflectivity of the substrate surface.

Further, the above-mentioned object is realized by a surface inspection apparatus comprising a light source for irradiating a light on the surface of a substrate, means for focusing a scattered light from the substrate surface, and detector means for detecting the scattered light focused by the focusing means, characterized in that the surface inspection apparatus is provided with means for correcting a detection sensitivity of the detector means on the basis of a reflectivity of the substrate surface.

DETAILED DESCRIPTION OF THE INVENTION

The present invention will be described in detail in connection with preferred embodiments with reference to attached drawings.

First Embodiment

Figure 1:
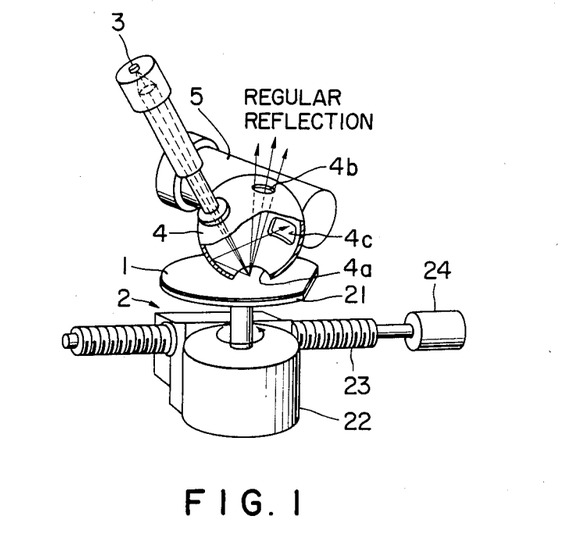
FIG. 1 is a perspective view illustrating a first embodiment of a surface inspection apparatus according to the present invention.
Figure 2:
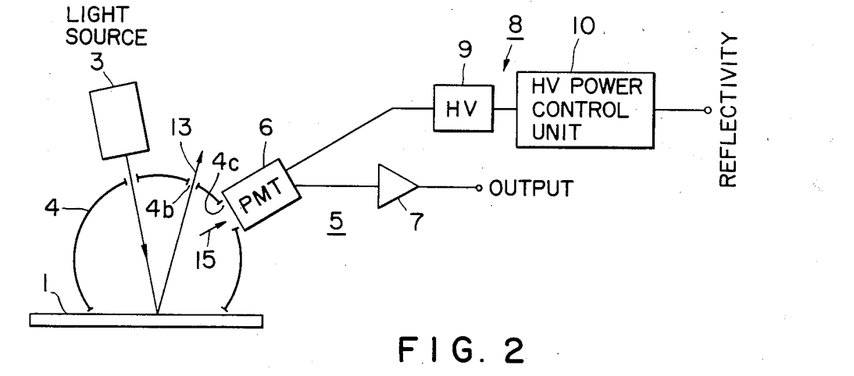
FIG. 2 is a schematic view diagrammatically showing an optical system and detection circuit arrangement associated therewith which are employed in the surface inspection apparatus shown in FIG. 1.

Initially, referring to FIGS. 1 and 2, there is shown a first embodiment of a surface inspection apparatus according to the present invention. A substrate 1 e.g. a semiconductor wafer etc. is laterally moved and rotated on a horizontal surface by a drive mechanism 2. The drive mechanism 2 comprises a turn table 21 on which the substrate 1 is mounted, a motor 22 for rotating the turn table 21, a rack 23 for laterally moving the motor 22 and the turn table 21, and a motor 24 for rotating the rack 23. By making use of these members, an operation is carried out to scan the whole surface of the substrate 1, thus to make a search for portions to be inspected.

The surface inspection apparatus for inspecting or examining the substrate 1 comprises a light source 3 for irradiating a light e.g. a laser beam etc. to a portion to be inspected of the substrate 1, a focusing means 4 for focusing a scattered light 15 produced due to reflection of the light from the light source 3, a detector means 5 for detecting the scattered light thus focused, and a correction means 8 for correcting a detection sensitivity of the detector means 5. The focusing means 4 is configured as an integral spherical body of which the lower end portion facing the substrate 1 is cut laterally. The integral spherical body 4 is provided at the upper portion thereof with a window 4b for guiding toward the outside only a reflected light 13, which impinges on the surface of the substrate 1 and is regularly reflected therefrom, and is provided at the side portion thereof with a focusing window 4c for focusing the scattered light 15 which impinges on particles attached on the substrate 1 and is scattered thereby. On the integral spherical body 4, material of barium system is painted. At the focusing window 4c, there is provided a photosensitive area of the detector means 5 adapted so that the scattered light 15 from the particles is incident thereto. As shown in FIG. 2, the detector means 5 in this embodiment comprises a photomultiplier tube (which will be simply called a "PMT" hereinafter) 6 provided at the focusing window 4c of the integral spherical body 4 to detect a scattered light, and a head amplifier 7 for amplifying a scattered light signal detected by the PMT 6. To the head amplifier 7, a known measurement indication device (not shown) is connected and its output which has undergone indication processing is displayed. The correction means 8 is operative to correct the detection sensitivity of the PMT 6 constituting the above-mentioned detector means 5 on the basis of the reflectivity of the substrate 1. In this embodiment, such a corrective operation is made by controlling a voltage applied to the PMT 6 by a high voltage power supply unit (HV) 9 with a high voltage power control unit 10 on the basis of the reflectivity of the substrate 1. Namely, the high voltage power control unit 10 stores therein a program for setting a sensitivity in conformity with the reflectivity of the substrate used, thus making it possible to suitably select a voltage applied to the PMT 6 in accordance with the kind of the substrate 1.

A method of inspecting the surface of a substrate using the apparatus thus configured will be now described, wherein correction is made such that curves B, C and D shown in FIG. 18 become in conformity with the curve A.

Figure 3:
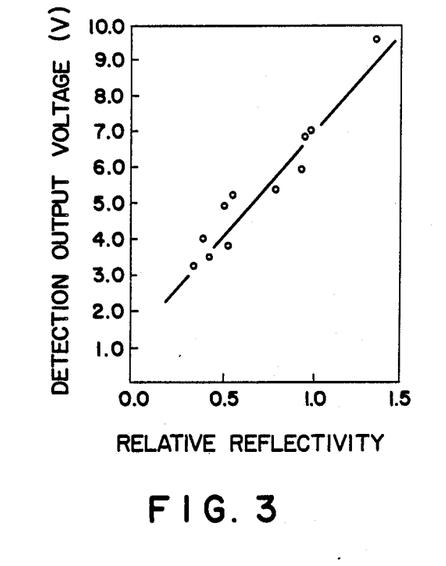
FIG. 3 is a graph showing detection output voltage versus relative reflectivity.
Figure 4:
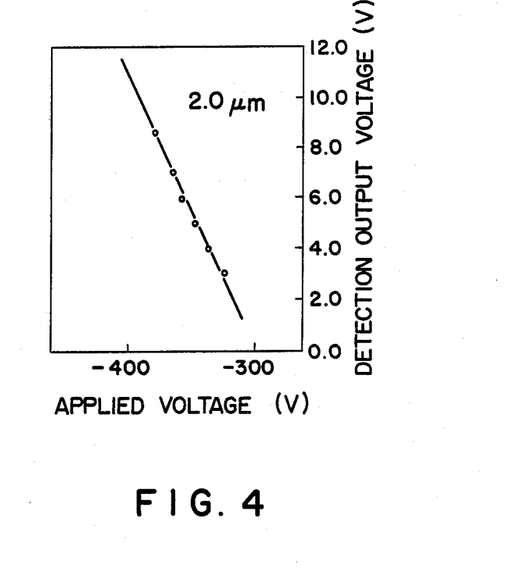
FIG. 4 is a graph showing detection output voltage versus applied voltage.
Figure 5:
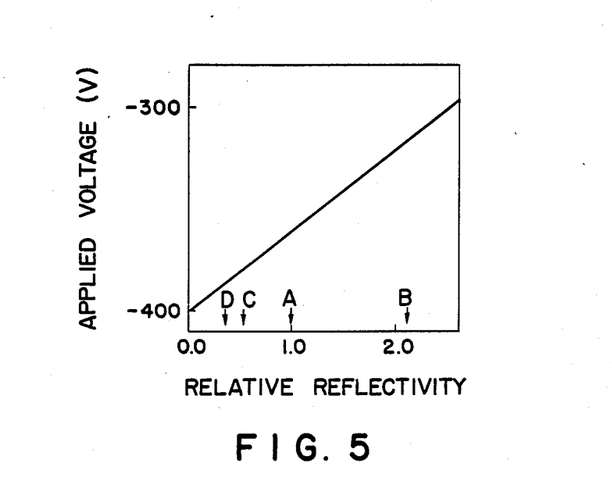
FIG. 5 is a graph showing applied voltage versus relative reflectivity.
Figures 6, 7:
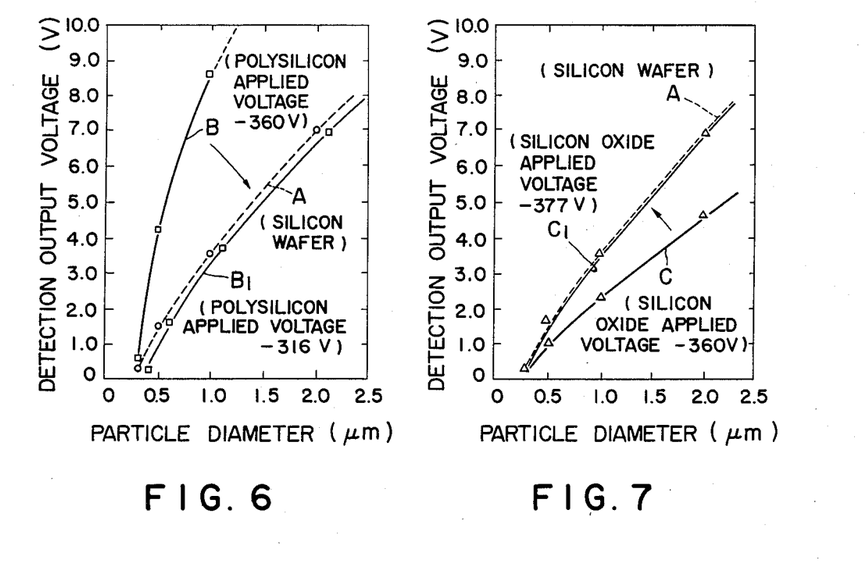
FIGS. 6 to 8 are graphs showing how detection output voltages of various substrates vary when the applied voltage is adjusted, respectively.
Figure 8:
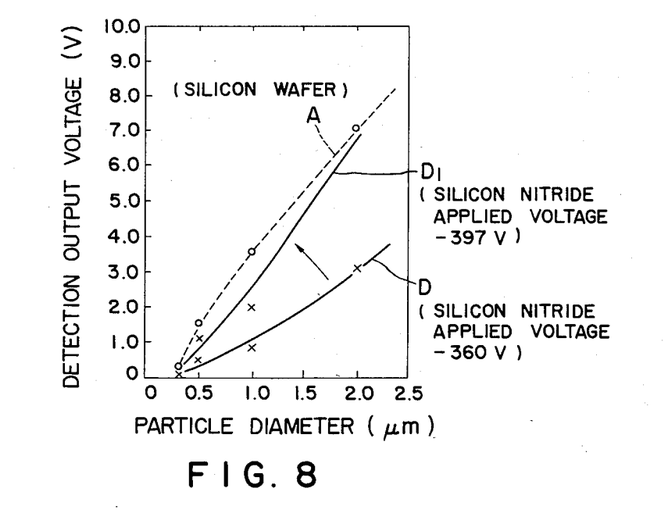

In this example, substrates on which a polysilicon thin film, a silicon oxide thin film and a silicon nitride thin film are respectively coated are used, and standard particles having a diameter of 2 μm are attached on the respective substrates. FIG. 3 is a graph obtained by plotting each relationship between a reflectivity and an output voltage when the substrates configured as stated above are employed. As seen from this figure, the reflectivity of a reflected light from the standard particles linearly increases with respect to the output voltage. Referring to FIG. 4, there is further shown a relationship between an output voltage when standard particles having the same diameter as stated above are employed and a voltage applied to the PMT 6. It is seen that this relationship is linear. Accordingly, as shown in FIG. 5, a relationship between a relative reflectivity and an applied voltage to the PMT is obtained from these relationships. FIG. 5 is a graph useful for allowing a sensitivity characteristic of a substrate in which reflectivity is changed due to the fact that a thin film is coated thereon to be in conformity with the sensitivity characteristic of the substrate of the silicon wafer on which a thin film is not coated. When a relative reflectivity with respect to the silicon wafer is known, a voltage to be applied to the photomultiplier 6 can be seen from FIG. 5. For instance, with respect to an applied voltage of −360 volts when the substrate A of the silicon wafer is used, the relative reflectivity when the substrate B on which a polysilicon thin film is coated is used is about 2.1 as shown in FIG. 5. Accordingly, an adjustment is made such that an applied voltage to the PMT 6 is equal to −316 volts. Thus, the curve B changes to a curve $B_l$ as shown in FIG. 6. As a result, the curve $B_l$ becomes in conformity with the curve A obtained with the silicon wafer substrate. Accordingly, in this case, when an adjustment is made by using the correction means 8 such that an applied voltage to the PMT 6 is equal to −316 volts, an output voltage PMT 6 becomes equal to an output thereof when the substrate of the silicon wafer is used, thus making it possible to judge the diameter of the particle in the same manner. Further, when the thin film is formed with a silicon oxide, a voltage (−377 volts) to be applied can be seen from an arrow C in FIG. 5. By making an adjustment of an applied voltage in this way, the curve C in FIG. 7 changes to a curve $C_l$, thus making it possible to be in conformity with the curve A obtained with the substrate of the silicon wafer. In addition, when the thin film is formed with a silicon nitride, by using FIG. 5 in the same manner as stated above, an adjustment is made such that an applied voltage is equal to −397 volts, a curve $D_l$ substantially conforming to the curve A can be obtained as shown in FIG. 8. Accordingly, by making an adjustment of an applied voltage to the PMT 6 depending upon changes in the reflectivity in a manner stated above, it is possible to detect particles with the same sensitivity as in the substrate of the silicon wafer.

Second Embodiment

Figure 9:
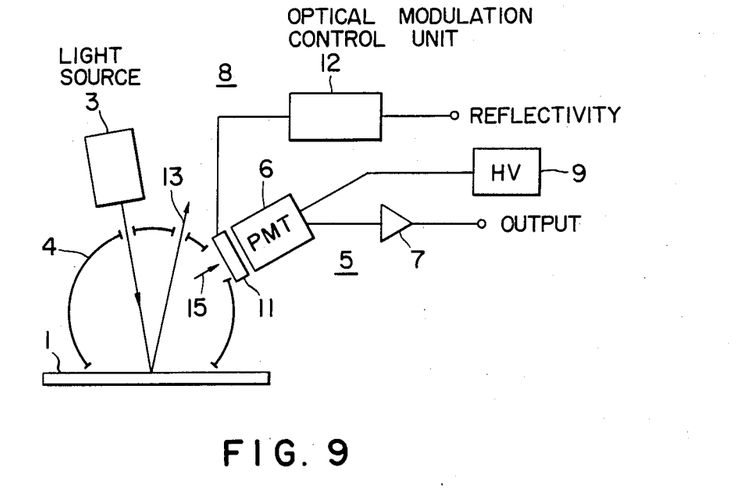
FIG. 9 is a block diagram schematically illustrating a second embodiment of a surface inspection apparatus according to the present invention.

FIG. 9 is a block diagram illustrating a preferred second embodiment of a surface inspection apparatus according to the present invention, wherein parts identical to those in the first embodiment are designated by the same reference numerals, respectively. The second embodiment is characterized in that an applied voltage to the PMT 6 is fixed and a filter 11 functioning to vary the ratio as the correction means is provided in front of the PMT 6. For this filter 11, an optical modulator or modulating device such as a liquid crystal is employed. An optical modulation control unit 12 coupled to the filter 11 adjusts an applied voltage to the liquid crystal 11 constituting the filter on the basis of a reflectivity of a substrate used, thereby making it possible to vary the light-screening ratio. Thus, this allows the detection sensitivity of the PMT 6 to be in correspondence with the sensitivity of the substrate of the silicon wafer. Accordingly, detection of the particles is possible in a manner similar to the above-mentioned embodiment. Instead of the light modulator, a plurality of ND filters may be replaced for changing light-screening ratio. In addition, a movable iris may be provided at the position of the filter 11 to adjust an amount of light incident to the PMT 6.

Third Embodiment

Figure 10:
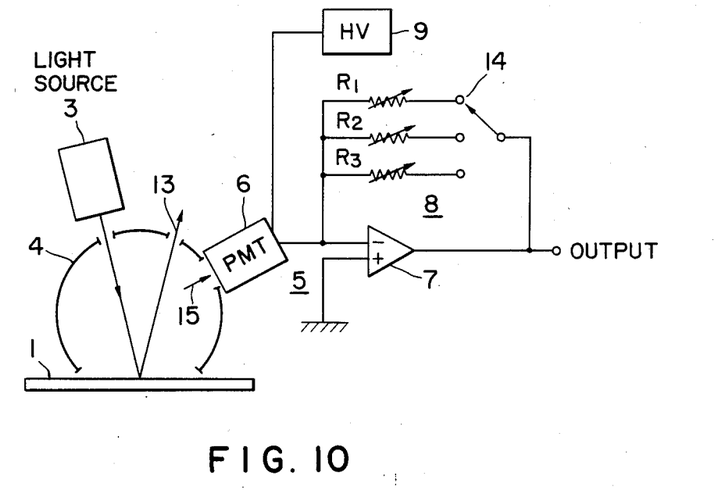
FIG. 10 is a block diagram schematically illustrating a third embodiment of a surface inspection apparatus according to the present invention.

FIG. 10 shows a preferred third embodiment according to the present invention. This embodiment is characterized in that the correction means 8 is provided in the head amplifier which amplifies a scattered light signal detected by the PMT 6. The correction means 8 in this embodiment is comprised of a changeover switch 14 in which a circuit comprising variable resistors $R_1$, $R_2$ and $R_3$ is incorporated, thus to adjust the amplification factor of a scattered light signal detected by the PMT 6. Such an adjustment can allow each sensitivity of substrates on which thin films are respectively coated to be in correspondence with the sensitivity of the substrate of the silicon wafer.

Fourth Embodiment

Figure 11:
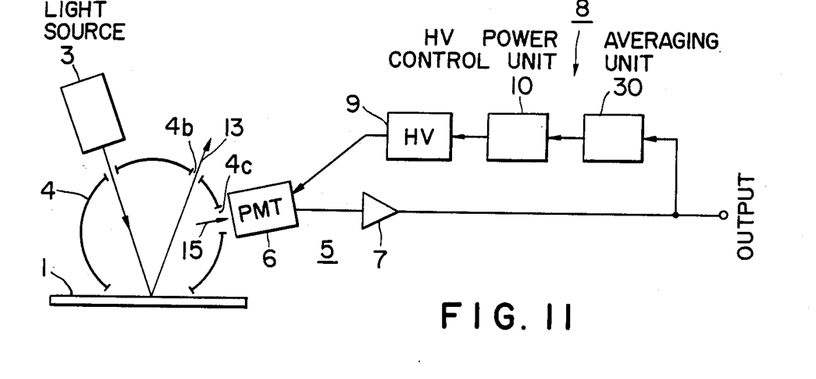
FIG. 11 is a block diagram schematically illustrating a fourth embodiment of a surface inspection apparatus according to the present invention.

FIG. 11 shows a block diagram illustrating a preferred fourth embodiment of a surface inspection apparatus according to the present invention. By using a laser beam emitted from the light source 3, scanning of the surface of the substrate 1 to be inspected is successively carried out. The regularly reflected light 13 from the surface of the substrate 1 travels from one opening portion 4b of the integral spherical body 4 toward the outside. The scattered light 15 produced due to the surface condition of the substrate 1 is integrated and the scattered light thus integrated travels from another opening portion 4c of the integral spherical body 4 toward the outside. The scattered light 15 thus guided is incident on a light-receiving surface of the PMT 6 and then is converted into a voltage signal corresponding to the intensity of light in the PMT. The voltage signal converted therein is amplified by the head amplifier 7 having a fixed amplification factor, and then is delivered to a measurement circuit (not shown). In this measurement circuit, a slice level corresponding to a particular particle diameter is set. The measurement circuit is operative to detect an output of the head amplifier 7 on the basis of the slice level, thereby to detect dust or rubbish having a diameter more than the particular particle diameter.

On the other hand, an output voltage from the head amplifier 7 is also delivered to an averaging unit 30. This averaging unit 30 is operative to average the output voltage of the head amplifier 7 for a predetermined time period to hold the output voltage thus averaged. The hold voltage of the average unit 30 is delivered to the high voltage power control unit 10. This high voltage power control unit 10 delivers a control signal corresponding to the hold voltage of the averaging unit 30 to the high voltage power supply unit 9. The high voltage power supply unit 9 is provided for supplying a dc high voltage to the PMT 6. The value of th dc high voltage is set in accordance with the control signal. The PMT 6, the head amplifier 7, the averaging unit 30, the high voltage power control unit 10 and the high voltage power supply unit 9 constitute an optical detection system for detecting intensity of a scattered light from the substrate 1.

Figure 12:
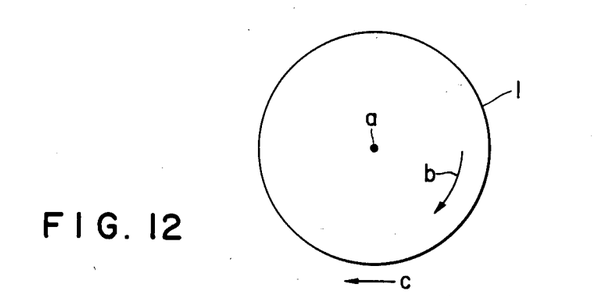
FIG. 12 is a plan view for explaining a laser scanning method employed in the surface inspection apparatus shown in FIG. 11.

Prior to carrying out detection of dust or rubbish etc. with the arrangement thus configured, first one irradiates a laser beam from the light source 3 to the surface of the substrate 1 for a predetermined time period to convert the scattered light 15 from the surface of the substrate 1 into a voltage signal corresponding thereto in the PMT 6. Thereafter one averages the voltage signal thus obtained in the averaging unit 30. Referring to FIG. 12, there is shown an example of a method of scanning a laser beam in this case wherein an operation is made to take the focus of the laser beam substantially at a central point of the substrate 1 to be measured thereafter to rotate the substrate 1 in a direction indicated by an arrow b in this condition and to parallel move it in a direction indicated by an arrow c. For instance, for a time period e.g. during one rotation of the substrate 1, a voltage signal converted in the PMT 6 is averaged in the averaging unit 30. A dc high voltage corresponding to the voltage signal which has undergone a holding operation in the averaging unit 30 is output from the high voltage power supply unit 9. Thus, the sensitivity of the PMT 6 is set to a value corresponding to a scattering factor of the surface of the substrate 1. The above-mentioned high voltage power control unit 10 is programmed in advance so that the level of a conversion voltage signal of the PMT 6 obtained when scanning the surface of the substrate 1 using the laser beam is kept constant independent of kinds of substrates to be measured.

After the sensitivity of the PMT is set, detection of particles attached on the surface of the substrate 1 is carried out. Namely, the surface of the substrate 1 is successively scanned by using the laser beam from the light source 3. Every scanning operation, the intensity of the scattered light 15 from the surface of the substrate 1 is detected by the PMT 6. A measurement circuit (not shown) detects an output of the head amplifier 7 on the basis of a slice level corresponding dust or rubbish etc. having a particular particle diameter to be detected, thereby to detect dust or rubbish etc. having a diameter larger than the particular particle diameter. Every time when the kinds of the substrates vary, a new setting of the PMT 6 is made in the same manner as stated above to correct the sensitivity of the entirety of the optical detection system, thereby making it possible to detect each scattered light from particles on the surfaces of substrates having different reflectivity with the same sensitivity.

Fifth Embodiment

Figure 13:
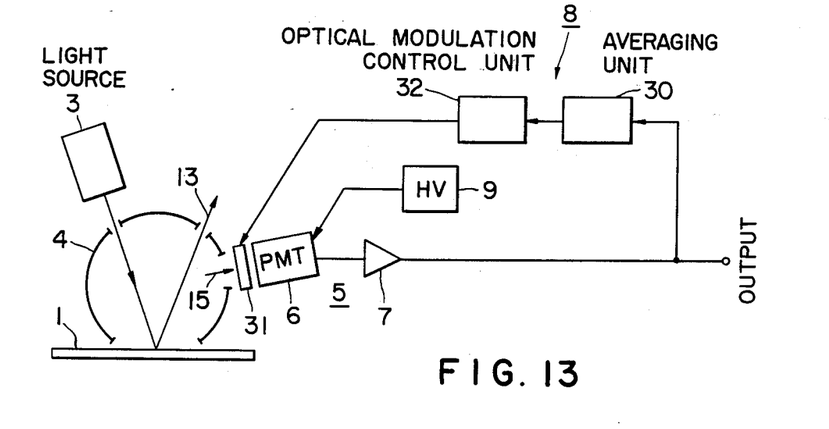
FIG. 13 is a block diagram schematically illustrating a fifth embodiment of a surface inspection apparatus according to the present invention.

FIG. 13 is a block diagram illustrating a preferred fifth embodiment of a surface inspection apparatus according to the present invention. This embodiment is characterized in that an optical modulator or modulating device 31 comprised of a liquid crystal is provided at a light-receiving surface of the PMT 6 to control this optical modulator 31 with an output of an optical modulation control unit 32 to vary a light-screening factor, thus to change the sensitivity of the entirety of the optical detection system. A hold voltage of the averaging unit 30 which averages an output of the head amplifier 7 is delivered to the optical modulation control unit 32. In the case of the apparatus of this embodiment, a constant dc high voltage is always supplied from the high voltage power supply unit 9 to the PMT 6, thus maintaining the sensitivity of the PMT 6 itself at a fixed value. The apparatus according to this embodiment varies a light-screening factor of the light modulator 31 in correspondence with intensity of the scattered light from the substrate 1, thereby to correct th sensitivity of the entirety of the optical detection system comprising the PMT 6, the head amplifier 7, the averaging unit 30, the high voltage power supply unit 9, the optical modulator 31 and the optical modulation control unit 32.

Sixth Embodiment

Figure 14:
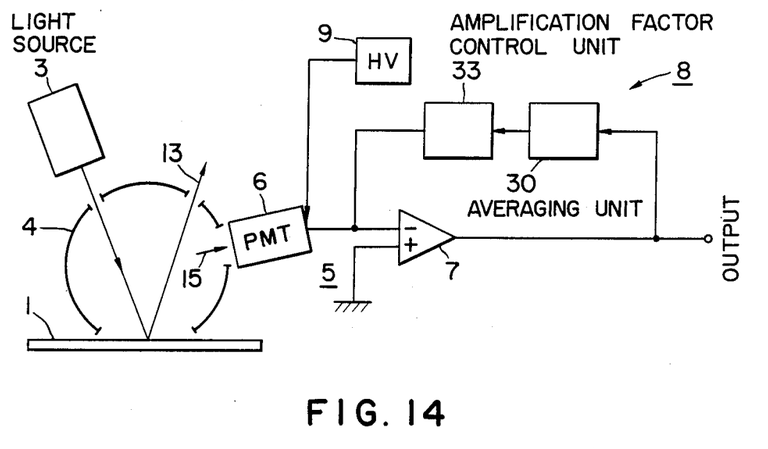
FIG. 14 is a block diagram schematically illustrating a sixth embodiment of a surface inspection apparatus according to the present invention.

FIG. 14 is a block diagram illustrating a preferred sixth embodiment of a surface inspection apparatus according to the present invention. In the apparatus of this embodiment, a constant dc high voltage is delivered from the high voltage power supply unit 9 to the PMT 6 at a fixed value. Instead, within a feedback loop of the head amplifier 7, an amplification factor control unit 33 which determines an amplification factor of the head amplifier 7 is provided, thus to control a resistance value of a feedback resistor provided in the amplification factor control unit 33 on the basis of a hold voltage of the averaging unit 30. Namely, by varying a resistance value of the amplification factor control unit 33 in accordance with intensity of a scattered light from the surface of the substrate 1 thereby to change the amplification factor of the head amplifier 7, each scattered light produced due to particles having the same diameter attached on the surfaces of the substrates having different reflectivity is obtained as a voltage signal of the same level.

Seventh Embodiment

Figure 15:
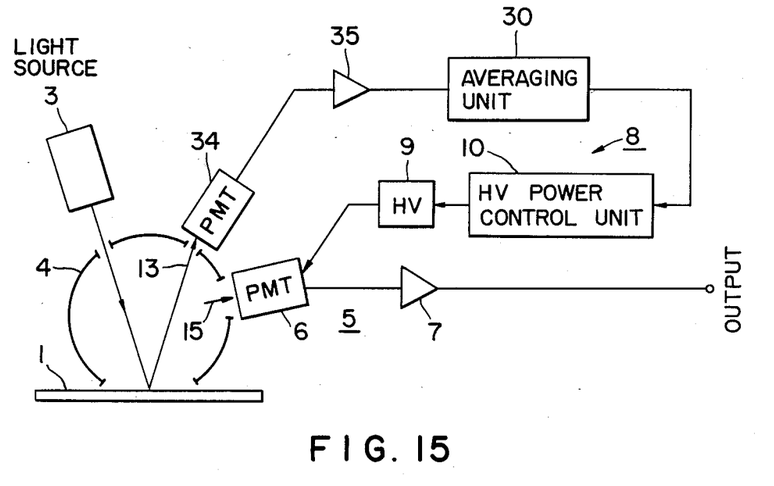
FIG. 15 is a block diagram schematically illustrating a seventh embodiment of a surface inspection apparatus according to the present invention.

FIG. 15 is a block diagram illustrating a preferred seventh embodiment of a surface inspection apparatus according to the present invention. In the abovementioned embodiments shown in FIGS. 11, 13 and 14, the detection sensitivity of the optical detection system is set in accordance with the intensity of the scattered light from the substrate surface. The apparatus in this embodiment is characterized in that the detection sensitivity of the optical detection system is set in accordance with the intensity of the regularly reflected light 13 from the substrate surface. The reason why such a setting is employed is that the intensity of the scattered light 15 and the intensity of the regularly reflected light 13 have a relationship such that they linearly increases with respect to the reflectivity of the surface of the silicon semiconductor substrate.

In the apparatus of this embodiment, another PMT 34 for measuring the intensity of the regularly reflected light 13 is newly provided. With this implementation, a voltage signal converted by the PMT 34 and proportional to the intensity of the regularly reflected light is amplified by a head amplifier 35, and then the voltage signal thus amplified is delivered to the averaging unit 30. Thus, the voltage signal which has been averaged and undergone a holding operation in the averaging unit 30 is supplied to the high voltage power control unit 10. Although not shown, a constant dc high voltage produced in a high voltage power supply unit is delivered to the PMT 34.

Eighth Embodiment

Figure 16:
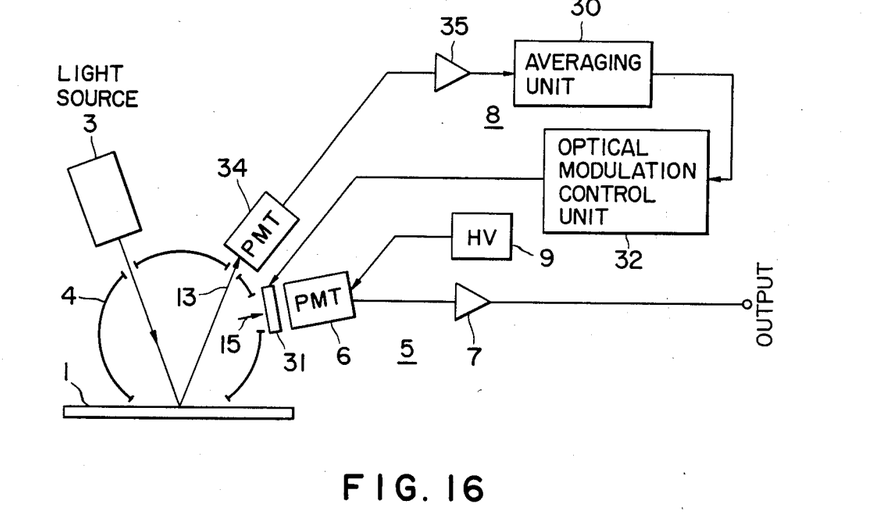
FIG. 16 is a block diagram schematically illustrating a eighth embodiment of a surface inspection apparatus according to the present invention.

FIG. 16 is a block diagram illustrating a preferred eighth embodiment of a surface inspection apparatus according to the present invention. The apparatus in this embodiment which is provided with the optical modulator 31 at the light-receiving surface of the PMT 6 to control the optical modulator 31 with an output of the optical modulation control unit 32 to vary the light-screening factor, characterized in that the detection sensitivity of the optical detection system is set in accordance with the intensity of a regularly reflected light from the substrate surface. In the apparatus of this embodiment, the PMT 34 for measuring intensity of the regularly reflected light 13 is also provided, and a voltage signal converted by the PMT 34 and proportional to the intensity of the regularly reflected light 13 is amplified by the head amplifier 35 and then is delivered to the averaging unit 30. The voltage signal which has been averaged and undergone hold operation in the averaging unit 30 is delivered to the optical modulation control unit 34. Also in this case, although not shown, a constant dc high voltage produced in a high voltage power supply unit is delivered to the PMT 34.

Ninth embodiment

Figure 17:
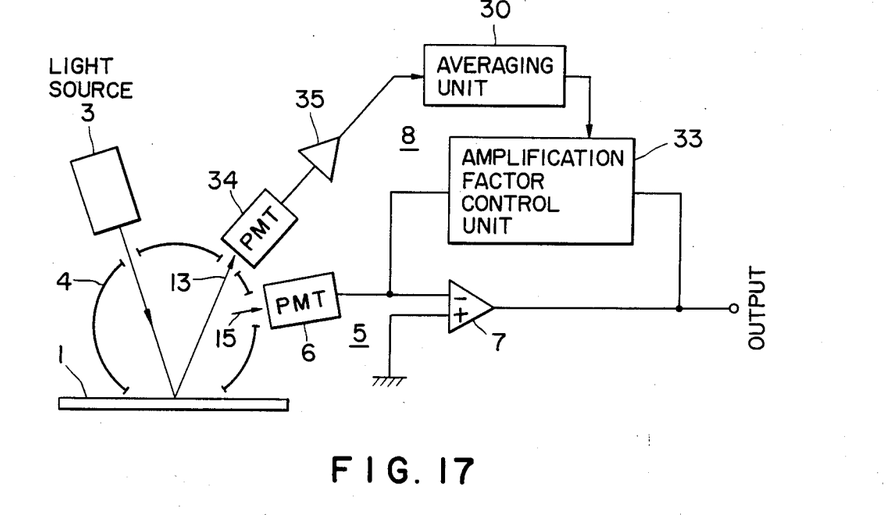
FIG. 17 is a block diagram schematically illustrating a ninth embodiment of a surface inspection apparatus according to the present invention.

FIG. 17 is a block diagram illustrating a preferred ninth embodiment of a surface inspection apparatus according to the present invention. The apparatus in this embodiment is configured so as to vary the amplification factor of the head amplifier 7 as shown in FIG. 14 to set the detection sensitivity, characterized in that the detection sensitivity of the optical detection system is set in accordance with the intensity of a regularly reflected light from the substrate surface. In the apparatus of this embodiment, the PMT 34 for measuring intensity of the regularly reflected light 13 is also provided, and a voltage signal converted by the PMT 34 and proportional to the intensity of the regularly reflected light is amplified by the head amplifier 35 and then is delivered to the averaging unit 10. Subsequently, the voltage signal which has been averaged and undergone a holding operation in the averaging unit 10 is delivered to the amplification factor control unit 33. Although not shown, constant dc high voltages produced in two high voltage power supply units are delivered to the two PMTs 6 and 34, respectively.

When a plurality of correction means stated above are used in combination, the present invention can provide the same advantages. In addition, the present invention is applicable not only to the inspection of the surface of a semiconductor wafer, but also to the inspection of surfaces of other substrates.

As stated above, the surface inspection apparatus according to the present invention is configured so as to correct the sensitivity of the detector means for detecting a scattered light in accordance with reflectivity of the substrate, thus making it possible to inspect the surface of a substrate with the same slice level and the same sensitivity even when materials of substrates, or kinds of thin films or thicknesses of thin films are different from each other.

What is claimed is:

1. A method of inspecting a substrate surface having a known reflectivity to detect the diameters of particles on the substrate surface, comprising the steps of:
   irradiating light on said substrate surface,
   collecting scattered light from said particles,
   detecting said scattered light collected, and
   compensating for detection sensitivity of said scattered light in accordance with a compensation control signal on the basis of intensity of said scattered light from said particles corresponding to reflectivity of said substrate surface so that the particle diameters on the substrates can be detected correctly even when the reflectivities of the substrate surface differ from a standard.

2. A method according to claim 1, wherein said correction control signal is obtained by averaging signals detected when said substrate surface is subject to scanning of said irradiating light.

3. A method of inspecting a substrate surface having a known reflectivity to detect the diameters of particles on the substrate surface, comprising the steps of:
   irradiating light on said substrate surface;
   collecting scattered light from said substrate surface,
   detecting said scattered light collected, and
   compensating for detection sensitivity of said scattered light in accordance with a compensation control signal on the basis of intensity of regularly reflected light from said substrate surface corresponding to reflectivity of said substrate surface so that the particle diameters on the substrates can be detected correctly even when the reflectivities of the substrate surface differ from each other.

4. A method according to claim 3, wherein said compensation control signal is obtained by averaging signals detected when said substrate surface is subject to scanning of said irradiating light.

5. An apparatus for inspecting a substrate surface, having a known reflectivity to detect the diameters of particles on the substrate surface, comprising:
   a light source irradiating light on said substrate surface,
   means for collecting scattered light from said particles,
   a photomultiplier tube for detecting said scattered light collected by said collecting means,
   a detector circuit for detecting an amplitude of said scattered light,
   means for outputting a compensation control signal corresponding to said reflectivity of said substrate surface on the basis of intensity of said scattered light from said substrate surface, and
   means for compensating for detection sensitivity of said photomultiplier tube in accordance with reflectivity of said substrate surface, so that the particle diameters on the substrates can be detected correctly even when the reflectivities of the substrate surfaces differ from each other.

6. An apparatus according to claim 5, wherein said compensation control signal outputting means is operative to output the compensation control signal obtained by averaging detection signals from said detector circuit.

7. An apparatus according to claim 5, wherein said compensating means is operative to compensate said detection sensitivity by adjusting an applied voltage to said photomultiplier tube.

8. An apparatus according to claim 5, wherein said compensating means is comprised of a filter having a variable light-screening factor provided in front of said photomultiplier tube.

9. An apparatus according to claim 5, wherein said compensating means is comprised of a movable iris provided in front of said photomultiplier.

10. An apparatus according to claim 5, wherein said compensating means is comprised of means for adjusting amplification factor of said detector circuit.

11. An apparatus for inspecting a substrate surface having a known reflectivity to detect the diameters of particles on the substrate surface, comprising:
    a light source irradiating light on said substrate surface,
    means for collecting scattered light from said substrate surface,
    a photomultiplier tube for detecting said scattered light collected by said collecting means, and
    a detector circuit for detecting amplitude of said scattered light,
    means for outputting a compensation control signal corresponding to said reflectivity of said substrate surface on the basis of intensity of a regularly reflected light from said substrate surface,
    a detector circuit for detecting amplitude of said scattered light,
    means for compensating a detection sensitivity of said photomultiplier tube in accordance with a reflectivity of said substrate surface, so that the particle diameters on the substrates can be detected correctly even when the reflectivities of the substrate surfaces differ from each other.

12. An apparatus according to claim 11, wherein said means for outputting a compensation control signal is provided with a second detector means for detecting a regularly reflected light from said substrate surface, said compensation control signal means being operative to output the compensation control signal obtained by averaging detection signals from said second detector means.

13. An apparatus according to claim 11, wherein said apparatus further comprises a second photomultiplier tube for detecting said regularly reflected light.

14. An apparatus according to claim 11, wherein said compensating means is operative to compensate said detection sensitivity by adjusting an applied voltage to said photomultiplier tube.

15. An apparatus according to claim 11, wherein said compensating means is comprised of a filter having a variable light-screening factor provided in front of said photomultiplier tube.

16. An apparatus according to claim 11, wherein said compensating means is comprised of a movable iris provided in front of said photomultiplier tube.

17. An apparatus according to claim 11, wherein said compensating means is comprised of means for adjusting the amplification factor of said detector circuit.

* * * * *